United States Patent
Feichtinger

(10) Patent No.: US 7,028,567 B2
(45) Date of Patent: Apr. 18, 2006

(54) PROCESS AS WELL AS DEVICE FOR MEASURING A COMPONENT AMOUNT RELEASED DURING A THERMO-CHEMICAL TREATMENT OF METALLIC WORK PIECE FROM THE GASEOUS ATMOSPHERE

(75) Inventor: Heinrich Feichtinger, Hinteregg (CH)

(73) Assignee: IPSEN International GmbH, (DE)

( * ) Notice: Subject to any disclaimer, the term of this patent is extended or adjusted under 35 U.S.C. 154(b) by 0 days.

(21) Appl. No.: 10/974,894

(22) Filed: Oct. 27, 2004

(65) Prior Publication Data
US 2005/0081602 A1  Apr. 21, 2005

Related U.S. Application Data

(62) Division of application No. 10/732,689, filed on Dec. 10, 2003.

(51) Int. Cl.
*G01N 33/00* (2006.01)

(52) U.S. Cl. ....................................... 73/866
(58) Field of Classification Search ............... 73/866.5, 73/865.8, 866, 787, 73; 33/783, 791, 787, 33/788, 789, 790, 805, 572
See application file for complete search history.

(56) References Cited

U.S. PATENT DOCUMENTS 2,756,590 A * 7/1956 Gehman et al. ............... 73/792
3,287,810 A * 11/1966 Heidenhain .................. 33/791
5,009,512 A * 4/1991 Lessi et al. .................... 374/6
5,251,498 A * 10/1993 Nakatsukasa et al. ...... 73/865.8
5,275,057 A * 1/1994 Alexander .................... 73/799
5,378,889 A   1/1995 Lawrence
5,425,279 A * 6/1995 Clark et al. ................. 73/865.8
5,589,650 A * 12/1996 Flemming et al. ............ 73/866
6,725,557 B1 * 4/2004 Kushibiki et al. ............ 33/555
6,817,238 B1 * 11/2004 Go Boncan et al. .......... 73/149

FOREIGN PATENT DOCUMENTS

EP         0558130         1/1993

* cited by examiner

*Primary Examiner*—Robert Raevis
(74) *Attorney, Agent, or Firm*—Cantor Colburn LLP

(57) ABSTRACT

The invention concerns a process for the measurement of the amount of a component that is released from a gaseous atmosphere during the thermo-chemical treatment of metallic work pieces. In order to provide a measurement system that offers the opportunity even in the ongoing treatment process for supplying the most exact data on the amount of a component released from the gaseous atmosphere and absorbed by the work piece a process is suggested with the invention for the continuous measurement of the amount of a component that is released from the gaseous atmosphere surrounding the work pieces and absorbed by the work pieces during a thermo-chemical treatment of metallic work pieces where a probe whose longitudinal extension significantly exceeds its width is exposed to the effect of the gaseous atmosphere, the longitudinal change of the probe over time in the longitudinal direction caused by the absorption of the component released by the gaseous atmosphere is measured and the measured longitudinal change is used for the determination of the amount of the transferred component transferred from the gaseous atmosphere to the probe.

14 Claims, 6 Drawing Sheets

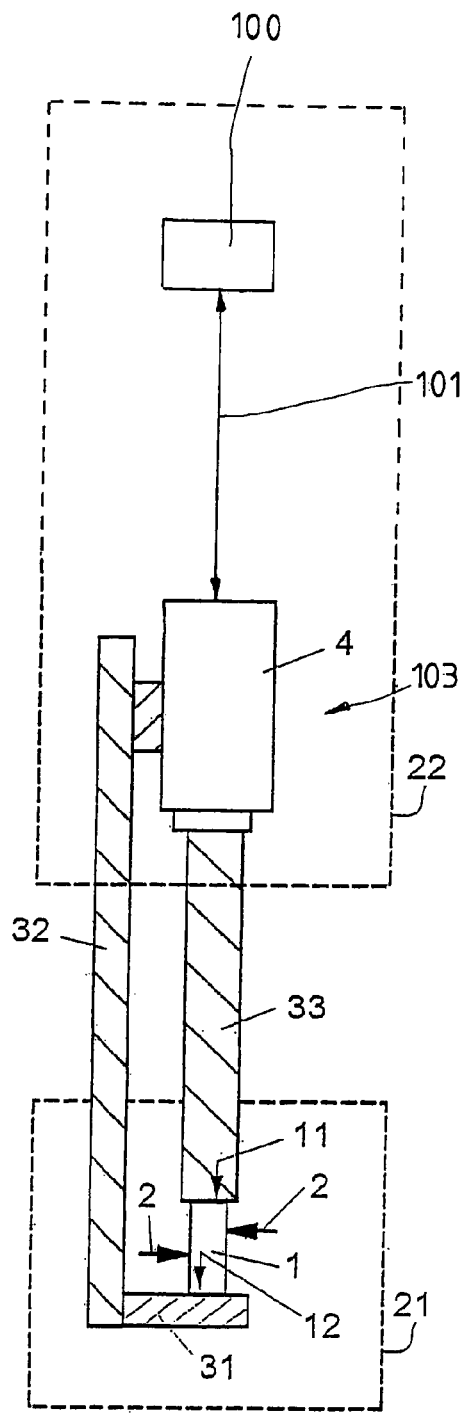
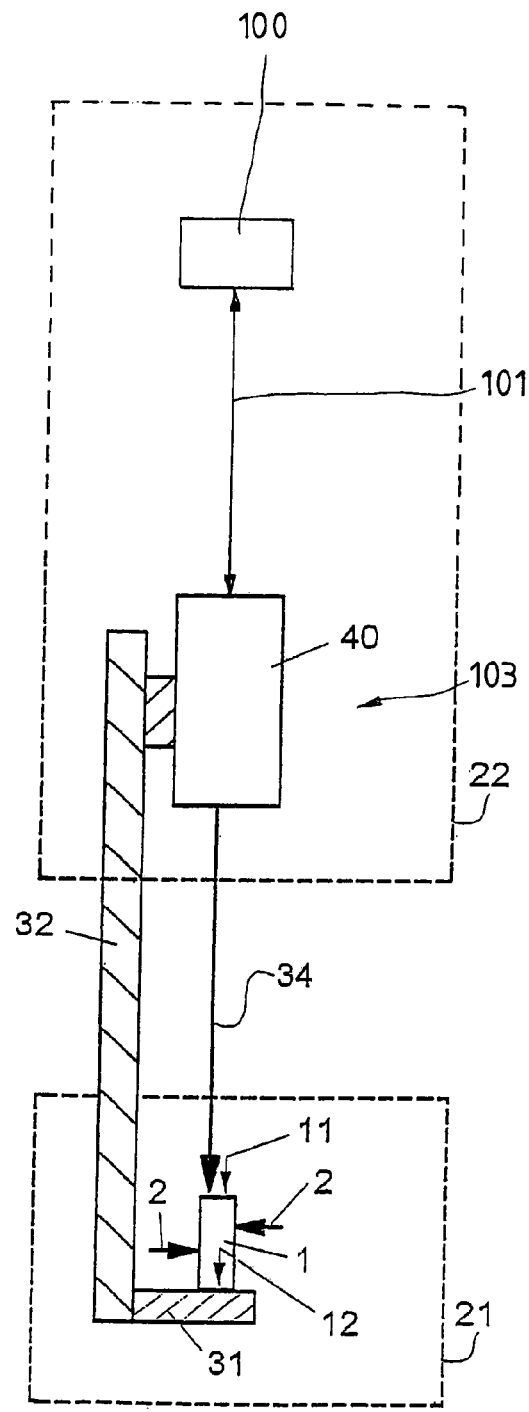
Fig. 7
Fig. 8

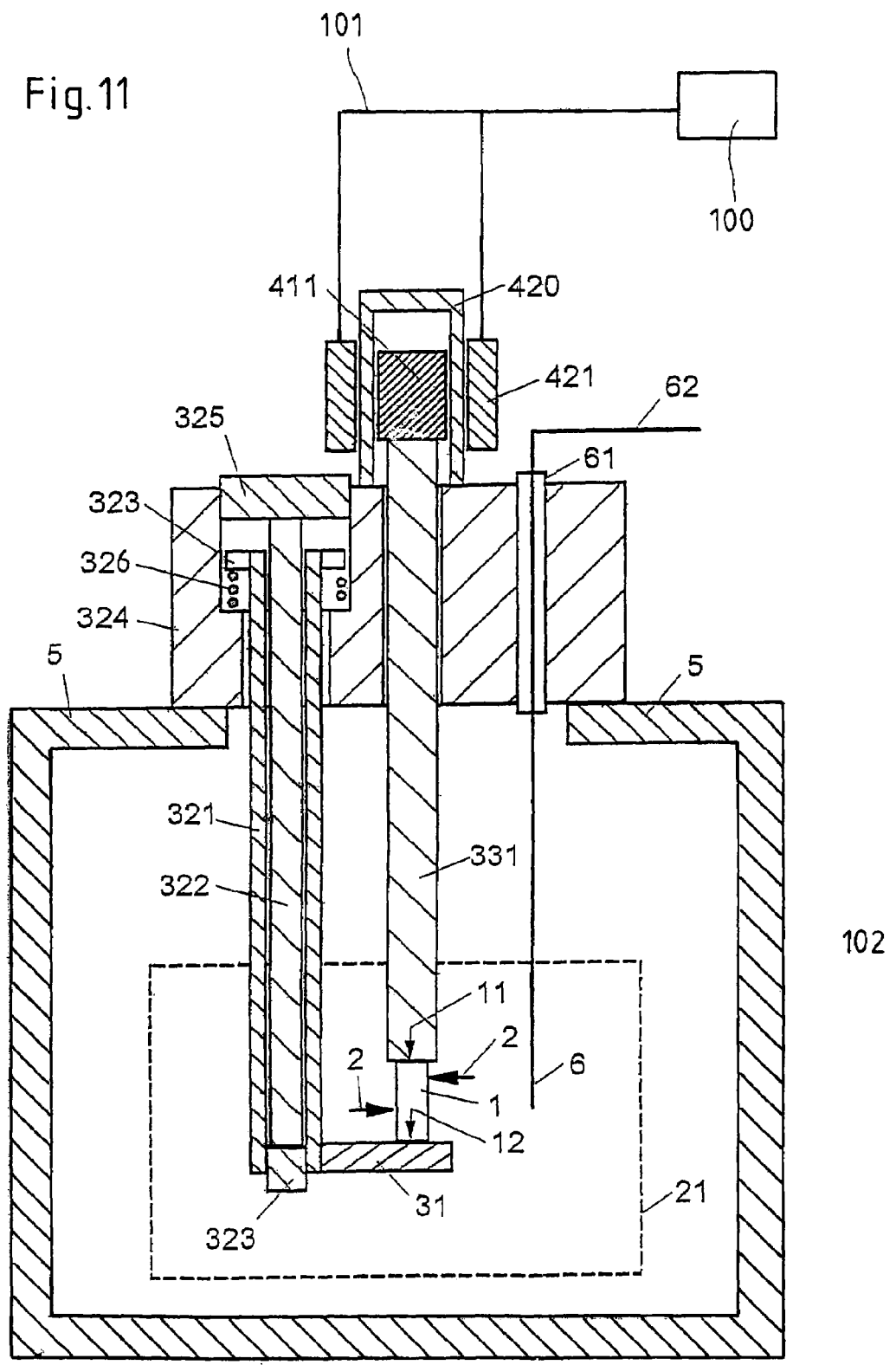

PROCESS AS WELL AS DEVICE FOR MEASURING A COMPONENT AMOUNT RELEASED DURING A THERMO-CHEMICAL TREATMENT OF METALLIC WORK PIECE FROM THE GASEOUS ATMOSPHERE

CROSS REFERENCE TO RELATED APPLICATION

This application is a divisional application of, and claims the benefit of, U.S. application Ser. No. 10/732,689 filed on Dec. 10, 2003, the entire contents of which are incorporated herein by reference in their entirety.

FIELD OF THE INVENTION

The invention concerns a process and a device for the measurement of the amount of a component that is released during a thermo-chemical treatment of metallic work pieces from the surrounding gaseous atmosphere and absorbed by the work pieces.

DESCRIPTION OF THE RELATED ART

Thermo-chemical processes, like for example case hardening, nitriding or carbonitriding, are of great importance because they allow to give a component special mechanical, physical and/or chemical characteristics in surface-near areas. A great number of thermo-chemical processes occurs under the influence of heat through the separation of one or more components from the gaseous phase, which consequently leads to the dissolution of soluble atoms of those components, e.g. carbon or nitrogen and the formation of compounds with parts of alloy elements of the work pieces, such as carbides, nitrides and carbonitrides.

Achieving the desired characteristics depends primarily on the geometry as well as the composition of the produced surface layer, meaning from the concentration profile, as well as the bond type of the component in the surface-near area. The concentration profile is the result of the composition, the temperature and the duration of the gas atmosphere impacting the component and can be set by appropriately selecting the parameters time, temperature, pressure, as well as gas composition.

Setting the above-mentioned parameters however in many cases cannot be performed with such accuracy that a sufficient statement can be made on the result of a thermo-chemical treatment. An important reason for this is that thermo-chemical processes take place in a strong imbalance and that the kinetics depends among other things also on the condition of the surface of the work piece to be treated. In addition, the convection situation in the reactor must be considered, as well as the presence of foreign reactive surfaces where the treatment gas reacts in an uncontrolled way.

In order to eliminate the above-mentioned disturbance variables at least in part by calculation, various measurement and evaluation methods especially in case hardening have been developed, which, however, have the disadvantage that they do not facilitate an exact prediction of the procedure.

In case hardening, for example, the work pieces to be treated are exposed to temperatures in the range of 900° to 1100° to a carbon-containing atmosphere. As carbon purveyor hydrocarbons, such as methane or propane can be used that emit carbon atoms to the metal surface at the operational temperature while forming hydrogen. As a consequence of the physical and chemical absorption, the carbon atoms are separated and penetrate then into the metal via a diffusion process, creating a concentration profile that forms the appropriate hardening profile after cooling. If oxygen carriers, such as carbon dioxide and/or water vapor are present in addition to the hydrocarbon, then the actual carburizing process takes place through carbon monoxide that has been formed through the reaction with the oxygen carrier. The actual carburizing reaction then takes place through the cleavage of the absorbed carbon monoxide molecule at the surface of the work piece releasing an oxygen atom. The speed of the cleavage process and the carburization of the peripheral layer are essentially determined through the removal of the oxygen from the surface. This can either take place through the reaction of the absorbed carbon monoxide molecule with another carbon monoxide molecule to carbon dioxide or through the reaction with a hydrogen molecule to water vapor, whereby the last reaction takes place very quickly. The newly formed water can be regenerated with freshly added hydrocarbon to carbon monoxide and hydrogen, thus closing the reaction cycle.

With the knowledge of the alloy composition and the carburization temperature, the measurements of the partial pressures of the carbon content can be calculated, which develops a balance. The carbon content is called a C-level. In the area of carbon activities of the carburization process, the water is almost totally disassociated meaning that the amounts of carbon monoxide and hydrogen can be assumed as constant. Thus, the low remaining hydrogen content can be assumed to be defining for the carbon activity, whereby the hydrogen content can be exactly determined e.g. with the dew point method of measurement.

In the analogous carburizing system carbon monoxide/carbon dioxide that corresponds to the Boudouard equilibrium, carbon dioxide is only present in low amounts in contrast to other gases, which determines the carbon activity. The determination of the low carbon amounts can take place through infrared gas analysis.

An additional method for the determination of the carbon activity results from the utilization of the equilibrium with oxygen using, for example, the ratio of hydrogen and water vapor determining the carbon activity, which is in balance with the partial pressure of oxygen at a certain temperature. The partial pressure of the oxygen can be determined by measurement with a solid electrolyte probe.

All the above-mentioned measurement processes that attempt to record the carburizing effect of the atmosphere presume that the atmosphere is in balance with the surface of the work peace to be treated. The effective carbon concentration that actually materializes at the metal surface during the process depends, however, on the one hand on the speed of the carbon supply from the atmosphere and on the other hand from the speed with which the carbon is diffused into the interior of the metal. Here it is decisive how fast the oxygen released during the diffusion process is removed from the surface. Furthermore, for the actually achieved carburization it is important whether the removal of the oxygen from the surface takes place through the reaction with carbon monoxide or with hydrogen. Likewise, the convection conditions in the reactor play an influential role.

The measurement of the changes in the gaseous composition in the reactor is, therefore, only an indirect and in many cases a disadvantageous method of an inexact description of the actual processes taking place on the surface of the work piece. The processes could be even more complex if a soot deposit takes place in the heat treatment oven through increased carbon activity or if part of the carburization gas is used to reduce the surface oxides of the work piece.

The known state of the art measurement and evaluation processes are, therefore, inappropriate to make sufficient predictions on the course of a thermo-chemical process.

Proceeding from this, it is the task of the invention to develop a measurement process that offers the possibility during an ongoing treatment process to make an assertion that is as exact as possible on the amount of a component that is released from a gaseous atmosphere and absorbed by a work piece.

SUMMARY OF THE INVENTION

For the solution of this problem it is suggested in the invention to use a process of continuous measurements during the thermo-chemical treatment of metallic work pieces of the amounts of a component in the surrounding gaseous atmosphere that is released and absorbed by the work pieces whereby a probe whose length significantly exceeds its width is exposed to the effect of the gaseous atmosphere and the longitudinal change over time of the probe in the longitudinal direction caused due to the absorption of component released from the gaseous atmosphere is measured and the measured change in length is used for the determination of the amount of the component that has been transferred from the gaseous atmosphere into the probe.

The process according to the invention is based on the technical tenet that the probe is subjected to a change in volume due to the absorption of a component originating from a gaseous atmosphere that manifests itself in the longitudinal direction of the probe as a change of length that can be directly recorded and that is used for the determination of the amount of a transferred component. The change of volume takes place through an expansion of an iron grid taking place with the inclusion of component atoms and/or through an elimination that the component forms with one or several alloy elements of the probe. The process suggested by the invention facilitates, therefore, the direct measurement of the amount of a component that has been transferred from the gaseous atmosphere that has the advantage in contrast to the known measurement and evaluation methods known from the state of art that the disturbance variables created by pressure, temperature, reactive surfaces and the like do not have any influence on the measured results. The process according to the invention makes the exact determination of the amount that is transferred to the probe and, therefore, to the work piece from the gaseous atmosphere possible. The determination of the amounts can be advantageously measured on a continuous basis opening up the possibility of a rather exact prediction as prognoses can be calculated in measured time sequences, which show only a small error rate due to the high precision of measurement of the process according to the invention.

To determine the longitudinal change the probe is clamped into an especially designed receptacle. The receptacle consists of two thrust bearings, whereby one thrust bearing is mounted at an exact position and the other thrust bearing is positioned relatively mobile on the opposite side of the fixed thrust bearing. Because of the longitudinal expansion of the probe located between the two thrust bearings one thrust bearing will shift in relation to the other thrust bearing. The offset distance of the two thrust bearings due to the longitudinal change of the probe corresponds to the total longitudinal change of the probe. The longitudinal change of the probe is caused by the absorption of a component originating from the gaseous atmosphere whereby the component is diffused into said probe vertically to the longitudinal axis of the probe. Associated with the diffusion of the component is a volume change of the probe that causes a change in the surface profile of the two end faces that are positioned vertically to the longitudinal axis of the probe. At the beginning the two end faces of the probe are even so that a temporary change in height of the surface profiles of the two end faces leads to an overall longitudinal change of the probe over time. The change in height of the surface profile over time and the resulting longitudinal change of the probe are used according to the process to determine the amount of the component transferred to the probe. The measured longitudinal change can be used as a directly measurable factor to determine the component amount that has been absorbed by the probe.

According to another characteristic of the invention, the probe and the work pieces are exposed to the effect of the gas atmosphere at the same temperature. This way the same the probe as well as the work pieces are subjected to the same starting conditions so that the conditions measured at the probe can be transferred to the work pieces that are to be treated without any corrective calculations. This is especially valid when an identical alloy is used for the probe as well as for the work piece. The probe can be placed directly in the oven space of the thermo-chemical treatment plant. The probe can be installed directly in the thermo-chemical treatment plant as an in-site sensor or C-current sensor. As an alternative the provision can be made to locate the probe outside of the treatment plant and to provide it with a stream of gas that is extracted from the treatment atmosphere.

According to another characteristic of the invention it can be provided that an isothermal process is performed. This process has the advantage that the probe is subjected to a change in length that is not influenced by temperatures. The determination of the amount of absorbed component can be performed simply without corrective calculations. As an alternative it can also be provided to perform the process during changing temperatures. This is especially necessary if the process of the treatment of metallic work pieces cannot be performed at just one temperature. The process with changing temperatures requires, however, a compensation for the additional longitudinal changes of the probe caused by the temperature changes by calculation. This requires an additional expenditure compared to the isothermal process but has the advantage to be able to use the process according to the invention also in such processes where different temperatures are used during the process.

According to another characteristic of the invention, it is provided that the value of the surface profile change in a defined cooling of the probe, preferably of the longitudinal change of the probe in the longitudinal direction, and/or that the temperature range of this change is used for the determination of the amounts and the distribution of the component to be transferred. It is well known that volume changes or longitudinal changes take place during the phase transformation from iron-based work pieces, for example from austenite to perlite, whose size and temperature range are linked with the amount and the distribution of the component transferred from the gaseous phase. In contrast to the known measurement and evaluation methods known from the state of art, the process according to the invention offers herewith the option to determine or predict not only the amount but also the distribution of a component amount transferred to a work piece or to the probe from the gaseous atmosphere. This is an advantage, especially with geometrically complex components as exact predictions can be made on the enrichment of the component originating from the gaseous atmosphere also in those areas that are geometrically difficult to access. A concentration profile can, of course, also be determined or predicted by using the process according to the invention.

According to another characteristic of the invention it is provided that the material transfer to the probe takes place analog to the transfer to the work pieces. This can be achieved by placing the probe directly into the oven close to the work pieces or, if the probe is located outside of the oven that analog stream and temperature conditions are provided to the probe.

According to another characteristic of the invention, the gaseous atmosphere containing the component flows by the probe and/or the work piece with a defined flow rate. This process variation advantageously supports the process with the consequence that a comparably more precise measurement of the longitudinal change of the probe and a more exact determination of the transferred component amount can be made.

According to another characteristic of the invention, the transfer of the component only takes place through the outer shell if a tubular probe is used. In order to achieve this, the inner coat of the tubular probe could, for example, be covered or provided with a face layer that is impermeable for the component.

According to another characteristic of the invention it is provided that carbon is used as the component. Then the probe serves as a "C-sensor" or C-probe" and facilitates the determination of the carbon amount that is transferred during a carburization process from an added carbon carrier to the probe originating from the gaseous atmosphere and, therefore, to the work pieces to be carburized.

In reference to the device serving as a solution to the above described problem, a device is provided for the continuous measurement of the amount of a component that is released from the surrounding gas atmosphere and absorbed by the work pieces during a thermal treatment of metallic work pieces, comprising a receptacle of a probe whose longitudinal dimension far exceeds its width, by a longitudinal measurement system to record a temporary longitudinal change of the probe in the longitudinal direction and a computer.

A receptacle is provided for the probe. The receptacle serves the secure fastening of the probe within the gaseous atmosphere. A longitudinal measuring system 103 hereinafter "measuring system" or "measurement system") is attached to the receptacle that serves the recording of the temporary longitudinal change of the probe within the receptacle. The longitudinal change of the probe in the longitudinal direction is measured. The longitudinal change recorded by the longitudinal measurement system is supplied to a computer 100, 101 (hereinafter "computer" or "computer unit") that determines the amount of the component transferred to the probe from the gaseous atmosphere using predetermined arithmetic steps. The use of the device according to the invention makes it advantageously possible to determine the amount of the transferred component using the directly measurable geometric size of the probe so that disturbance values that lead to a falsification of the measurement results in indirect measurement and evaluation methods known in the state of art can be eliminated by the use of the device according to the invention. With the use of the device according to the invention exact measurements and therefore exact predictions can be made with respect to the amount of a component absorbed by the probe or the work pieces from the gaseous atmosphere.

According to another characteristic of the invention it is provided that the receptacle for the probe has two thrust bearings, whereby one thrust bearing is fixed in its position relative to its position to the longitudinal measurement system. The first thrust bearing cannot be moved relative to the longitudinal measurement system and the second thrust bearing that can be moved relative to the first thrust bearing as well as relative to the longitudinal measurement system. The probe held in the receptacle is held on the front by the two thrust bearings. At the start of the thermo-chemical process the front sides of the probe are even and abut the respective thrust bearings. During the process a volume change of the probe takes place due to the absorption of the component originating from the gaseous atmosphere, which also leads to change of the surface profile at the two faces of the probe abutting the thrust bearings. The change of the surface profile is expressed by the temporary change of height of the initially flat frontal faces leading to an expansion of the probe also in the longitudinal direction due to the enrichment of the component originating from the gaseous atmosphere in the probe. This longitudinal change in the longitudinal direction causes the offset of the relatively mobile thrust bearing. This offset of the bearing is recorded by the longitudinal measurement system and transferred to a computer that converts the recorded longitudinal change of the probe on the basis of a predetermined arithmetical rule to determine the amount of the absorbed component.

According to another characteristic of the invention at least a part of the receptacle for the probe is located within the gaseous atmosphere. This measure guarantees that the probe is exposed as much as possible to the same gaseous atmosphere than the work pieces to be treated. Preferably the whole receptacle including the probe is located within the gaseous atmosphere.

According to another characteristic of the invention the longitudinal measurement system is located outside of the gaseous atmosphere or at least outside the heated area of the gaseous atmosphere. Such a design has the advantage that it is not exposed to the temperature within the gaseous atmosphere or the pressure therein. Falsification of the measurement results caused by outside influences can be excluded advantageously.

According to another characteristic of the intervention, the longitudinal measurement system is an optically functioning longitudinal measurement system. Preferably a longitudinal measurement system functioning with a laser is used that delivers especially precise measurement results. As alternative it can also be provided that a mechanically functioning longitudinal measurement system can be used, which has the advantage in contrast to optically functioning system to be less interference prone to outside influences.

According to another characteristic of the invention a flow channel is provided for the probe. A tube 104, as shown in FIG. 8a, for example, could be used for the flow channel where the probe could be located. The use of the flow channel has the advantage that a defined flow environment can be created for the probe that facilitates a more exact determination of a measurement result.

According to an additional characteristic of the invention a temperature sensor is provided. It serves the determination of the possibly changing temperature during the process within the work pieces and the changing atmosphere surrounding the probe. The longitudinal changes resulting from the temperature changes of the probe can be recorded with the determined temperature values and can be transmitted to the connected computer for corrective calculations. The determination of the amounts of the transferred component is the result of the measured longitudinal change of the probe on the one hand and the determination of additional longitudinal changes of the probe caused by the temperature change on the other hand.

In reference to the probe, it is suggested according to the invention to use a probe for the continuous measurement of the amount of a component that is released from the gaseous atmosphere surrounding the work pieces and absorbed by the work pieces during a thermal-chemical treatment of metallic work pieces whose length by far exceeds its width.

Such a geometric design of the probe has the advantage that the volume change caused by the component absorbed from the gaseous atmosphere can be noticed especially in reference to the longitudinal expansion, leading to an advantageously simplified process. Preferably a probe in the form of a rod or a tube should be used. In order to prevent in the case of a tubular shaped probe that an inner shell absorbs the component from the gaseous atmosphere it can be equipped, if necessary, with a face layer that is impermeable for the component originating from the atmosphere.

BRIEF DESCRIPTION OF THE DRAWINGS

Additional advantages and characteristics of the invention can be found in the description of the following Figures. They show:

FIG. 7: the device according to the invention in a schematic presentation following the first design example FIGS. 8 and 8a: the device according to the invention in a schematic presentation following the second design example FIG. 11: the device according to the invention as a schematic presentation following a third design example.

DETAILED DESCRIPTION

Figure 1:
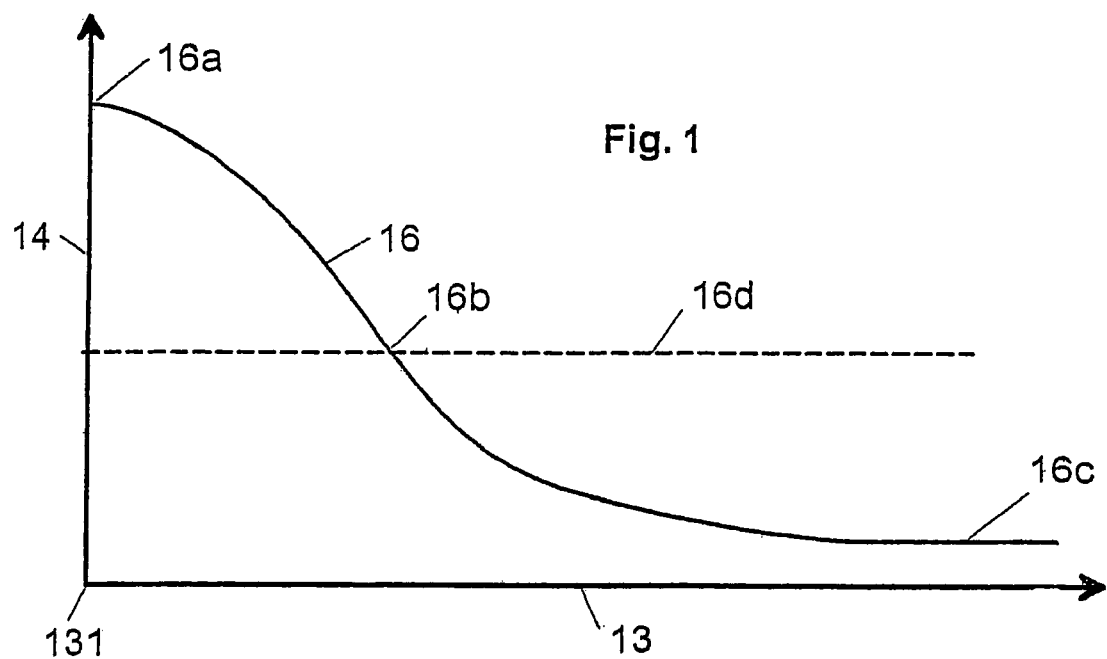
FIG. 1: a diagram of the concentration profile

FIG. 1 shows the progression of concentration profile 16 of a probe in the form of a graph in a sectional view vertical to the longitudinal direction of the probe. The position coordinate is designated 13 and the concentration coordinate is designated 14. The intersection of the position coordinate 13 and the concentration coordinate 15 is designated with 131 and corresponds in reference to the position coordinate 13 to the margin 9, that is the shell of the probe.

As can be clearly seen from the course of the concentration profile 16, the profile starts at a maximum marginal concentration 16a and decreases with the progressive position coordinate 13 to a value 16c, which essentially corresponds to the starting concentration of the probe before the thermo-chemical process. Point 16b designates the intersection between the profile curve of the concentration profile 16 and the mean value 16d of the concentration profile 16 in reference to the marginal concentration 16a and the starting concentration 16c.

Within the framework of a thermo-chemical process for the treatment of metallic work pieces, one component, for example carbon, is released from the gaseous atmosphere and transferred to the metallic work piece. The inclusion of atoms on the interstice in the metal grid of the work piece leads to a grid expansion, which in turn leads to a volume addition on a macroscopic level. This volume addition is approximately proportional to the absorbed concentration. This volume addition can be recognized as a linear extension in the longitudinal direction in a probe whose longitudinal extension significantly exceeds its width. If this longitudinal change is compared with the original length, the result is a relative extension of the probe as a function of the added concentration change.

Figure 2:
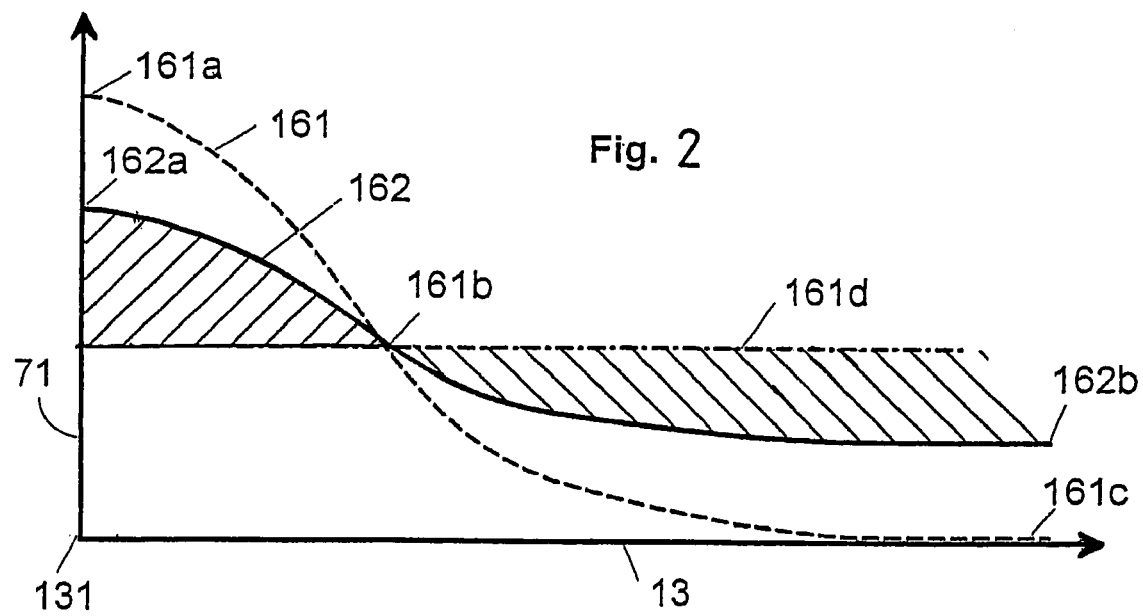
FIG. 2: a diagram of the longitudinal profile

FIG. 2 shows the longitudinal profile of the probe along the position coordinate 13 under the assumption of a linear-elastic conduct pursuant to curve 161 as it would appear in a probe under the assumption that its individual layers would be freely mobile in relation to each other. The proportionality between relative extensions on the one hand and the component absorption on the other hand results in a longitudinal profile 161 that is proportional to the concentration profile 162. At the margin, meaning the outer area of the shell of the probe, a maximum relative length 161a is set whereby the original length 161c in the inside of the probe remains unchanged. The chain dotted line 161d corresponds to the mean value of the relative longitudinal change.

The curve shown in FIG. 2 assumes hypothetically that the individual layers of the probe are mechanically freely mobile. In reality the individual layers however are connected, meaning that they cannot be set freely in their length according to the local concentrations of the absorbed component and cause thereby shear stress. The location designated 161b in FIG. 2 identifies the neutral fiber, meaning this line of the probe where the pressure load of the enriched marginal area devolves into the tensile stress of the interior probe. The hypothetical profile in FIG. 2 of the relative longitudinal change 161 is deformed by the effect of the shear stress in relation to the effective profile of the longitudinal change 162, meaning that the maximum elongation 161a is reduced by the influence of the pressure loads to the elongation value 162a while the minimum relative extension 161c is increased by the tensile stress to the value 162b.

Figure 3:
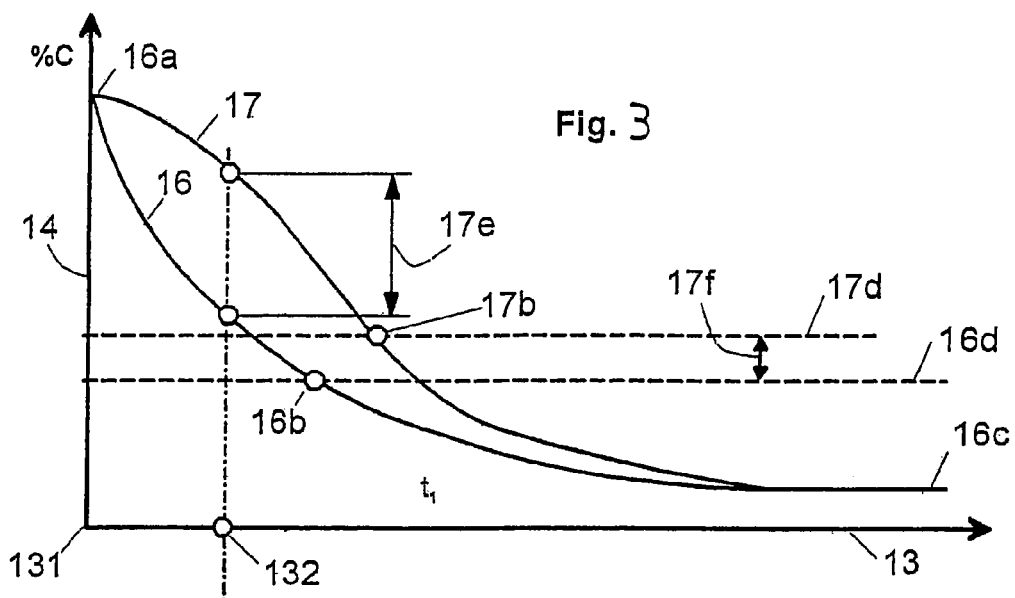
FIG. 3: a diagram of the concentration profile under the assumption of a plastic conduct at time t1
Figure 4:
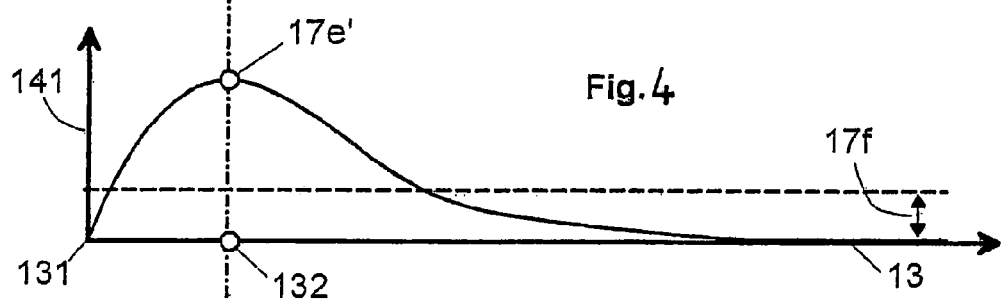
FIG. 4: a diagram of the concentration profile under the assumption of a plastic conduct at time t2

A fully plastic conduct is assumed in FIG. 3 to 4. FIG. 3 shows the concentration profile 16 at the time t1 and the concentration profile 17 at a later time t2. 16a designates the constant marginal concentration of the profile and 16c corresponds to the initial value before the start of the diffusion that is present within the probe at these two times. 16b and 17b designate the location where the median concentration set in according to the dotted graphics 16d and 17d at the two times. The coordinate 132 corresponds to the location of the maximum concentration change 17e between the two times t1 and t2.

The diagram according to FIG. 4 shows the local concentration change according to axis 141 between the two times t1 and t2 along the position coordinate 13 that is in the diffusion direction transverse to the longitudinal direction of the probe. The dotted line 17f corresponds to the increase in the average concentration between those two times.

Figure 5:
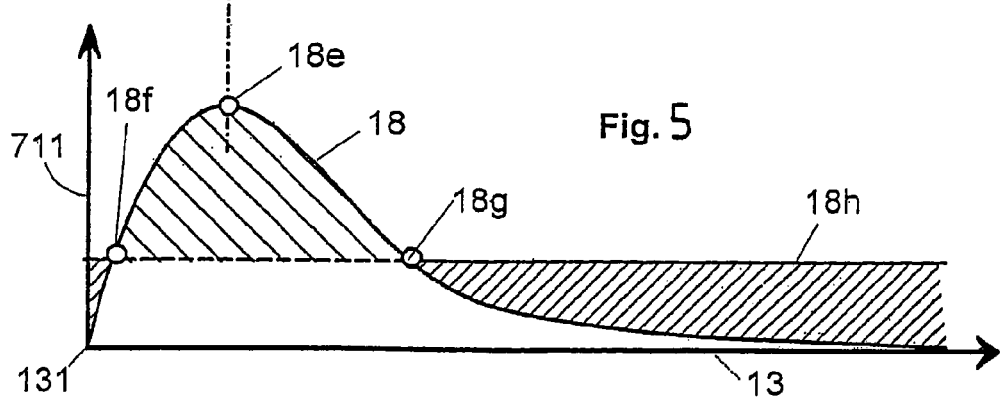
FIG. 5: a diagram of a concentration profile according to a first process step

In order to understand the diagram according to FIG. 5, where the axis 711 designates the relative longitudinal change, it is assumed that the initial profile of the probe length at time t1 is even, meaning that it is dissimilar to the example that has been shown in the fully-elastic case of the FIGS. 1 and 2 and the profile is leveled under the influence of the continuous shear stress during the diffusion. If this relaxation process between the times t1 and t2 would be momentarily "frozen," it would result in a profile of a longitudinal change following curve 18 according to FIG. 5, whereby the maximum relative longitudinal change 18a would occur at the coordinate value 132, which would lead to the formation of a pressure load zone. The negative shear stress at the points 18g and 18h on both sides of the zones change over to a positive shear stress. The pressure load zone as well as the two shear stress zones are shown in different hatchings.

Figure 6:
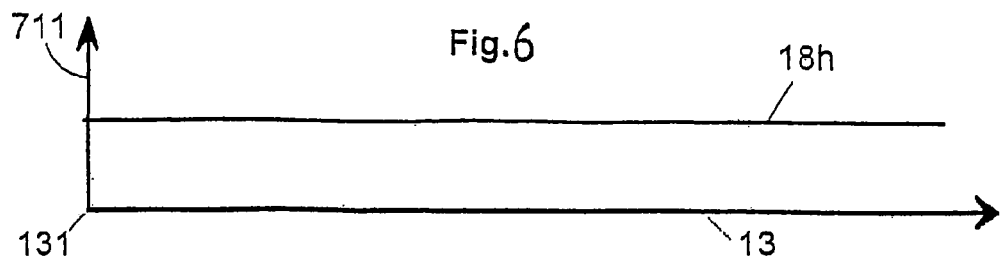
FIG. 6: a diagram of a concentration profile according to a second process step

The diagram, according to FIG. 6, shows the second step of the relaxation of the relative longitudinal profile 18, according to FIG. 5. The areas of the profile under pressure load are lowered, while the other areas are increased; whereby a common final level is set according to the average value 18h of the longitudinal profile across the common surface.

In reality, the process steps that are separated in FIGS. 5 and 6 take place simultaneously, meaning the relaxation superimposes the different local longitudinal change of the profile. As a result of this process, a uniform longitudinal expansion of the probe takes place, which is proportional to the totality of the absorbed component amount or to the average value of the concentration profile at that point in time. In practice, the change of the frontal profile of the probe or its longitudinal change during the thermo-chemical process that occurs at high temperatures, like the carburization process, is close to the fully-plastic conduct. During thermo-chemical processes that are conducted at lower temperatures, as is the case in nitration, the share of the elastic conduct rises.

FIG. 7 shows, for example, a device for conducting the process, according to the invention, while using a mechanical longitudinal measurement device 4. The probe 1 is situated under the atmosphere and at the temperature of the thermo-chemical process in the zone 21. The gaseous atmosphere that releases the component acts from all directions according to arrows 2 onto the shell of the probe 1. The probe rests with its lower face surface 12 on the thrust-bearing plate 31 that is connected via a fixture 32 with the longitudinal measurement device 4 in such a way that a relative mobility of the thrust bearing plate 31 and the longitudinal measurement device 4 is prevented. During the component diffusion, a longitudinal change of the probe 1 takes place in the longitudinal direction. The longitudinal change is transmitted via the highest points of the surface profile of face surfaces 11 and 12 to the rod 33, which, in turn, transmits it to the longitudinal measurement device 4.

The longitudinal measurement device 4 can be, for example, a capacitative or an inductive measurement system that transfers the measurement values to an electronic data processing system that is not shown in the figures. The longitudinal measurement device 4 is located within a zone 22 that is outside of the zone 21.

Figure 8A:
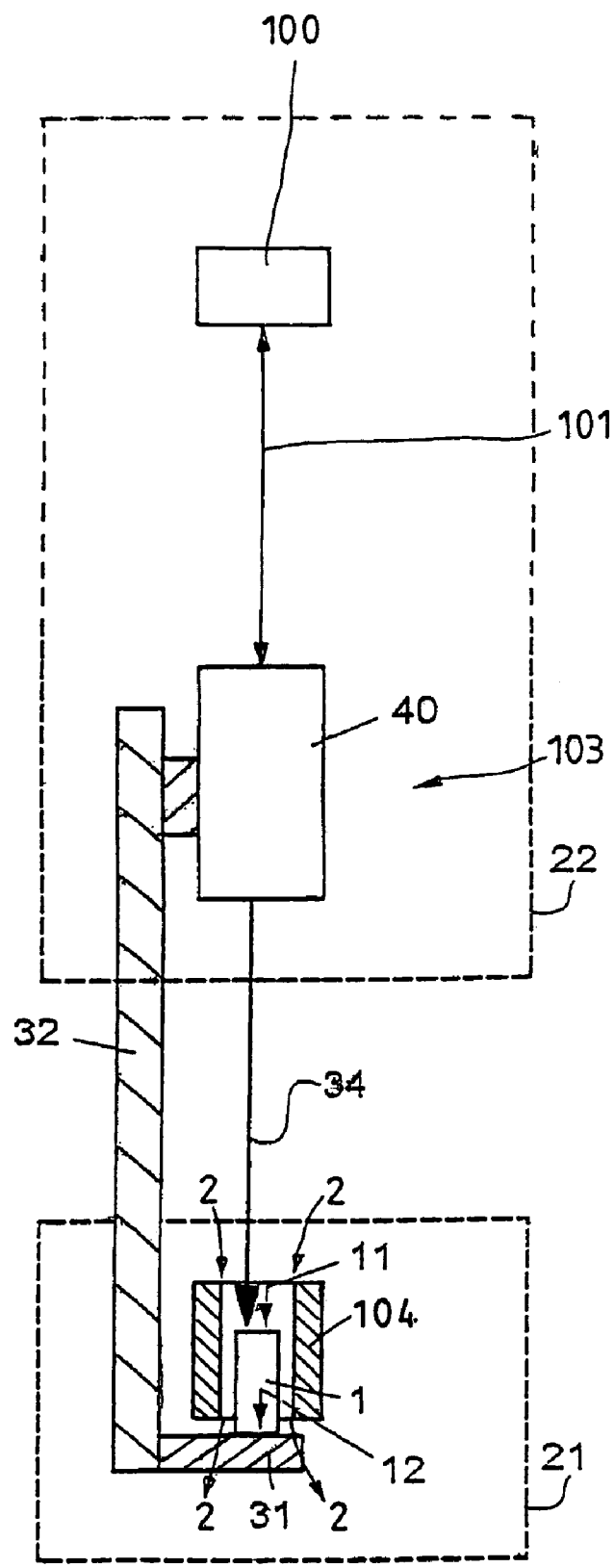

FIG. 8 shows an appropriate arrangement of the device according to the invention with the use of an optically-functioning longitudinal measurement device 40. Here, identical parts in comparison to FIG. 7 have the same numbers. The arrow 34 corresponds here to the measurement rod 33 according to FIG. 7 and represents the measurement beam of the optical system that could be, for example, in the form of a laser beam.

An additional measurement method to record the longitudinal change of the probe 1 is achieved by the use of strain gages. They are fixed in the longitudinal direction of the probe and simultaneously experience the longitudinal change of the probe shell. The expansion value that is compensated by the temperature can also be forwarded to data processing for an evaluation of the measured longitudinal change.

Figure 9:
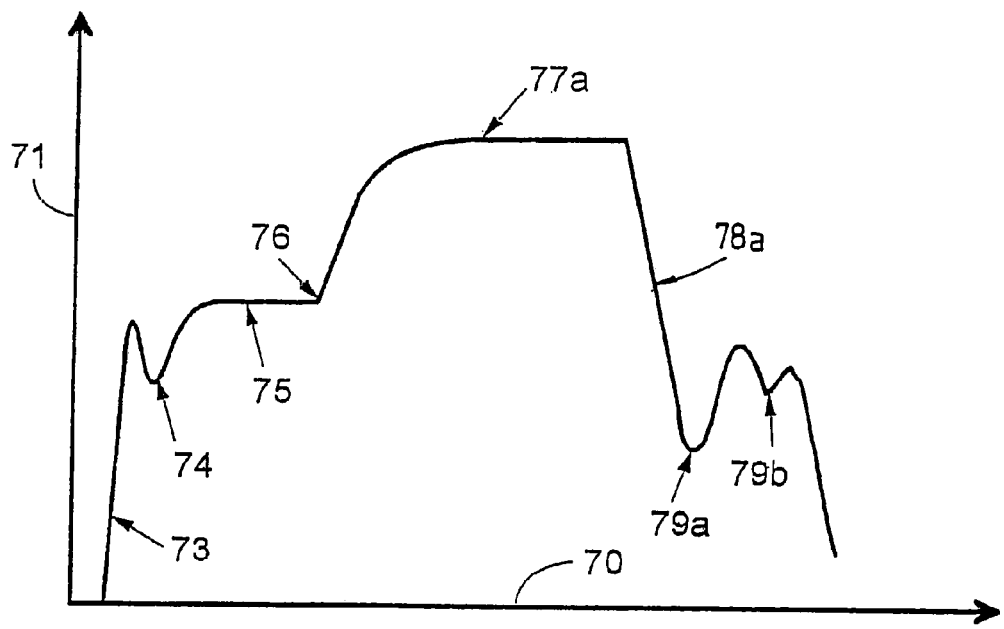
FIG. 9: a diagram of the temporary longitudinal change of a probe

FIG. 9 shows a typical diagram of the longitudinal change of a probe over time as it is measured, for example, with a process configuration according to FIG. 7 during the carburization of a steel Ck15 probe. The arrow 70 represents the time axis and arrow 71 the axis of the longitudinal change. The curve 73 designates a longitudinal change that takes place during the heating process in an inert gaseous atmosphere and follows the conversion of the initial structure whereby the structure is converted to austenite according to point 74. The curve 75 corresponds to the expansion up to the temperature constant. Up to this moment, the expansion curve corresponds to the usual dilatometric measurement curve.

At point 76, the inert gaseous atmosphere is replaced by a carburizing atmosphere, for example, by a mixture of carbon monoxide, hydrogen, and propane. An extension of the probe is seen immediately, which is transformed after a sufficiently long treatment time into the saturation of the curve 77a. At this juncture, the concentration in the entire probe is in balance with the carbon activity of the gaseous atmosphere. It is assumed in the presented example that the saturation is close to the solubility limit of carbon in austenite, meaning at the line Azm of the meta-stabile ion carbon diagram.

The curve 78a corresponds to the cooling of the probe whereby the elimination of the secondary cementite starts at point 79a and the elimination of the perlite starts at point 79b. It is assumed in the present example that the saturation point is in the supereutectoid area. If, however, the saturation of the probe lies in the subereutectoid area, point 79a would correspond to the elimination of ferrite.

In carburization tests that do no lead up to the saturation balance with the gaseous atmosphere, where the carburized gaseous atmosphere is, for example, replaced by inert gasses, the curve breaks off suddenly after point 76 and does not reach the saturation plateau 77a and changes almost immediately into a horizontal line. As at that point a profile that declines from the outside to the inside is present in the probe, the longitudinal change of the curve corresponds in a similar way to the cooling analogous to points 79a and 79b of the superimposition of the conversions of different carbon-containing alloys.

Figure 10:
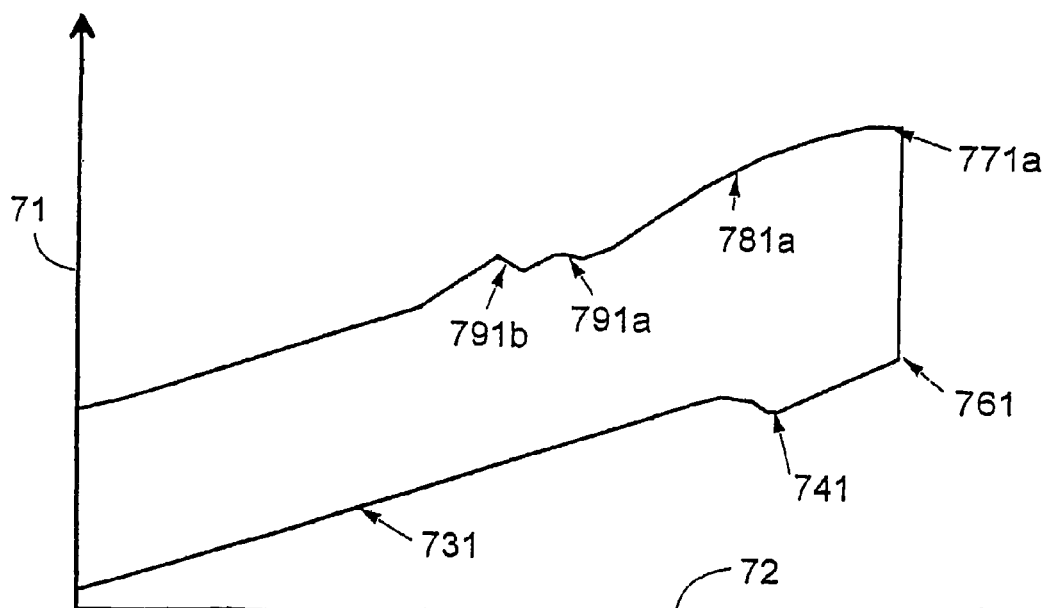
FIG. 10: a diagram of the longitudinal change via the temperature

FIG. 10 shows the above-described tests in a diagram of the longitudinal changes versus the temperature. The arrow 72 represents the temperature axis and the arrow 71 the relative longitudinal change.

The curve area 731 to 791 represents the heating of the probe in an inert atmosphere, whereby the conversion to austenite is concluded at point 741. Between the points 761 and 771a the isothermal longitudinal change follows, which goes back to the carburization process. The curve 771a–781a–791a–791b corresponds to the cooling of the probe after carburizing with conversions at point 791a and 791b.

FIG. 11 shows an exemplary device for the measurement of the longitudinal change of a probe corresponding to the process according to the invention. Here the probe 1 rests with its face surface 12 on a thrust bearing plate 31 and abuts with the other face surface 11 the rod 331 that presents a second thrust bearing relative to the probe 1. The probe 1 is exposed to high temperatures during the thermo-chemical process while the actual longitudinal measurement device can be optionally mounted on a cooled flange 324 that in turn is located in a gas-proof manner at the wall 5 of the thermo-chemical reactor 102 and is exposed to a temperature level close to room temperature creating a steep temperature gradient. The longitudinal changes of the probe are therefore superimposed by the longitudinal changes of the rod 331 and the structure of the thrust-bearing plate 31. In order to keep these disturbance values as low as possible, the rod 331 consists of ceramic, such as silica glass. It is especially important here that the face surface of the silica glass rod that is in contact with the face surface 11 of the probe is completely even and that its diameter exceeds that of the probe in order to make sure that all points of the face surface 11 are in contact with the face surface of the silica glass rod.

In order to compensate for the small, but due to their length still existing longitudinal changes of the rod 331 in the temperature gradient, the distance of the thrust-bearing plate 31 is set against the flange 324 by the rod 322, which preferably consists of the same ceramic material as the rod 331. As ceramic materials have a brittle reaction during mechanical loads, the thrust-bearing plate 31 is arranged on a high temperature-resistant metal pipe 321 that presses with a metal ring 323 against a compression ring 325 that is located in a bore 326 of the block 324. The ceramic rod 322 that is tightly connected below via the metal pipe 321 with the thrust-bearing plate 31 is therefore adjusted against the metal bolt that is connected at the face surface with the block 324. The great expansion of the metal pipe 321 during the temperature changes thus only has an effect on the changed compression of the spring 325 while the distance of the thrust-bearing platform 31 to the metal block 324 is determined by the less-changed position of the ceramic rod 322.

The actual longitudinal measurement in the example takes place inductively according to FIG. 11 as the ceramic rod 331 has a cylindrical metal body 411 on the top whose displacement is recorded by the inductive measurement coil 421 through the wall 420.

In addition, a temperature sensor 6 is provided, such as a shell thermal element that is led via a passage 61 through the flange 324 and is connected to data processing via a connection 62. The measurement values of the longitudinal measurement device and the temperature sensor are fed to a data recording device that is not shown and then are converted with the appropriate electronic computer program into a concentration profile of the component in the probe.

An important advantage of the process is the fact that the diffusion geometry changes the boundaries within broad ranges and that the activity and the time period of the controlled thermo-chemical process can be adjusted, e.g., by a pipe with a wall thickness of 0.1 mm to a cylindrical solid body with a diameter of 6 mm and more. In addition, the alloy of the probe can be selected in concordance with the material of the batches that are to be controlled so that the results of the measurement can be transferred directly to the conduct of the batch.

Using the example of a case-hardening process, the control process according to the invention will be shown in the following:

A process of one-dimensional non-stationary diffusion can be assumed in shorter carburization times, almost independently from the shape of the work piece. This is also valid for the probe if the wall thickness of the probe is sufficient, e.g., with a solid cylinder with a sufficiently large diameter. The diffusion coefficient for a certain material is a material constant if the temperature is known, with which the diffusion profile can simply be calculated if the carbon marginal concentration is known. The marginal concentration is, in balance, a function of the carbon activity of the gaseous atmosphere that is calculated from the gas composition and converted via the solubility characteristic of the steel while using the activity coefficient of the alloy in a carbon concentration. The value of the material transfer coefficient of the carbon from the gaseous atmosphere into the surface of the metal grid however is not known. The profile can be calculated as follows: Based on the process according to the invention, the amount of carbon that has penetrated the test object in its totality is known at any time. This results directly in the carbon mass flow in reference to the time and surface unit. The device according to the invention is therefore a C-flow sensor with direct measurement. Based on known diffusion data, the diffusion coefficient of the carbon in the alloy is calculated using the Arrhenius equation for the existing temperature. The marginal concentration is determined by solving the non-stationary diffusion equation for cylindrical coordinates, which leads to the measured average carbon content with the known diffusion coefficient in the measured time. This marginal concentration is converted via a non-stationary equation into a concentration profile within the framework of the geometry of the work piece.

The processes described above in the example of case hardening can be applied correspondingly in other thermo-chemical processes, such as the nitrogenization process.

If the temperature varies within the framework of a carburization process, the change of the carbon content can therefore be exactly determined. For this purpose, the longitudinal change resulting in the observed temperature range based on the linear expansion coefficient of the austenite, is deducted from the total longitudinal change. The remaining amount of the longitudinal change corresponds to the relative amount of the carbon absorbed by the probe.

The invention claimed is:

1. Device for the continuous measurement of the amount of a constituent of a gaseous atmosphere, said constituent released by the gaseous atmosphere and absorbed by metallic work pieces arranged within said gaseous atmosphere during a thermo-chemical treatment of said metallic work pieces in a thermo-chemical reactor, the device comprising:
 a holder for a probe whose longitudinal extension exceeds its width, said holder comprises at least one abutment supporting the probe, said abutment located within the gaseous atmosphere of said thermo-chemical reactor, such that the probe is exposed to the constituent,
 a longitudinal measurement system located outside of said thermo-chemical reactor to measure the longitudinal change of the probe over time in the longitudinal direction during the thermal-chemical treatment of the work pieces; and
 a computer unit in communication with the measurement system.

2. Device according to claim 1 wherein the holder for the probe comprises with two abutments, wherein one abutment is fixed in its position relative to the longitudinal measurement system.

3. Device according to claim 2 wherein the longitudinal measurement system has an optically functioning longitudinal measuring system.

4. Device according to claim 2 wherein the longitudinal measurement system is a mechanically functioning longitudinal measurement system.

5. Device according to claim 2 further comprising a tube as a flow channel, the probe located within the flow channel.

6. Device according to claim 2 further comprising a temperature sensor wherein a part of the temperature sensor is located within the gaseous environment and exposed to the constituent with the probe.

7. System for the continuous measurement of the amount of a constituent of a gaseous atmosphere, said constituent released by the gaseous atmosphere and absorbed by metallic work pieces arranged within said gaseous atmosphere during a thermo-chemical treatment of said metallic work pieces in a thermo-chemical reactor, the system comprising:
- a probe with a longitudinal extension that exceeds its width;
- a holder for said probe, said holder comprises at least one abutment supporting the probe, said abutment located within the gaseous atmosphere of said thermo-chemical reactor, such that the probe is exposed to the constituent;
- a longitudinal measurement system located outside of said thermo-chemical reactor to measure the longitudinal change of the probe over time in the longitudinal direction during the thermal-chemical treatment of the work pieces; and
- a computer unit in communication with the measurement system.

8. System according to claim 7, wherein the holder for the probe comprises two abutments, wherein one abutment is fixed in its position relative to the longitudinal measurement system.

9. System according to claim 8, wherein the longitudinal measurement system has an optically functioning longitudinal measuring system.

10. System according to claim 8, wherein the longitudinal measurement system is a mechanically functioning longitudinal measurement system.

11. System according to claim 8, further comprising a temperature sensor.

12. System according to claim 8, further comprising a tube as a flow channel, the probe located within the flow channel.

13. System according to claim 7, wherein the probe comprises a rod.

14. System according to claim 7, wherein the probe comprises a pipe.

* * * * *